United States Patent
Kim et al.

(10) Patent No.: US 10,302,964 B2
(45) Date of Patent: May 28, 2019

(54) CONTACT LENS FOR COLLECTING TEAR OR DELIVERING DRUG, AND METHOD FOR MANUFACTURING THE CONTACT LENS

(71) Applicant: KOREA INSTITUTE OF SCIENCE AND TECHNOLOGY, Seoul (KR)

(72) Inventors: Jinseok Kim, Seoul (KR); Yong-Won Song, Seoul (KR); Ockchul Kim, Seoul (KR); Hyungdal Park, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/458,065

(22) Filed: Mar. 14, 2017

(65) Prior Publication Data

US 2018/0143453 A1    May 24, 2018

(30) Foreign Application Priority Data

Nov. 22, 2016    (KR) .......................... 10-2016-0155809

(51) Int. Cl.
*G02C 7/00* (2006.01)
*G02C 7/02* (2006.01)
(Continued)

(52) U.S. Cl.
CPC ............ *G02C 7/049* (2013.01); *A61K 9/0051* (2013.01); *B29D 11/00048* (2013.01);
(Continued)

(58) Field of Classification Search
CPC .... A61F 9/0017; A61F 9/0026; A61F 9/0009; A61F 9/0048; A61F 2/16; A61F 2/1601;
(Continued)

(56) References Cited

U.S. PATENT DOCUMENTS

| 2002/0075447 A1* | 6/2002 | Andino ................... G02C 7/04 351/159.02 |
| 2014/0055741 A1 | 2/2014 | Havenstrite et al. |

(Continued)

FOREIGN PATENT DOCUMENTS

| KR | 10-2005-0052442 A | 6/2005 |
| KR | 10-2005-0094836 A | 9/2005 |

(Continued)

OTHER PUBLICATIONS

Hiratani, Haruyuki et al. "Timolol uptake and release by imprinted soft contact lenses made of N, N-diethylacrylamide and methacrylic acid." Journal of Controlled Release 83.2 (2002): 223-230. (8 pages in English).

(Continued)

*Primary Examiner* — Mustak Choudhury
(74) *Attorney, Agent, or Firm* — NSIP Law (57) ABSTRACT

A contact lens for collecting tear or delivering a drug includes an inner lens placed on an eyeball, an outer lens provided at an outer side of the inner lens to overlap the inner lens, and a plurality of pillars disposed between the inner lens and the outer lens to form a space between the inner lens and the outer lens, wherein the contact lens has a plurality of interfacing ports for connecting a chamber with an outside of the contact lens.

15 Claims, 11 Drawing Sheets

(51) Int. Cl.
  *G02C 7/04* (2006.01)
  *A61K 9/00* (2006.01)
  *B29D 11/00* (2006.01)
  *B29K 83/00* (2006.01)

(52) U.S. Cl.
  CPC .. *B29D 11/00096* (2013.01); *B29D 11/00125* (2013.01); *B29K 2083/00* (2013.01); *G02C 2202/16* (2013.01)

(58) Field of Classification Search
  CPC .... G02C 7/02; G02C 7/04; G02C 7/042–049; A61K 9/0051; B29D 11/00125; A61B 5/0022; A61B 5/1121; A61B 5/1128; A61B 5/14507; A61B 5/1455; A61B 5/6821
  USPC ............ 351/159.02, 159.04, 159.33, 159.36, 351/159.38, 159.73; 424/427, 428; 427/164, 535; 600/309, 573; 604/290, 604/298
  See application file for complete search history.

(56) References Cited

U.S. PATENT DOCUMENTS

| | | | |
|---|---|---|---|
| 2014/0088381 A1 | 3/2014 | Etzkorn et al. | |
| 2017/0086668 A1* | 3/2017 | Francois | A61B 3/113 |
| 2017/0252019 A1 | 9/2017 | Kim et al. | |

FOREIGN PATENT DOCUMENTS

| | | | |
|---|---|---|---|
| KR | 10-2006-0082792 A | | 7/2006 |
| KR | 10-2007-0006904 A | | 1/2007 |
| KR | 10-1571467 B1 | | 11/2015 |
| KR | 10-2015-0135252 A | | 12/2015 |
| KR | 10-2016-0004311 A | | 1/2016 |
| TW | 200710466 A | | 3/2007 |
| WO | WO 2004/063773 A2 | | 7/2004 |
| WO | WO 2005/009297 A1 | | 2/2005 |
| WO | WO 2005/103678 A2 | | 11/2005 |
| WO | WO 2007/002671 A1 | | 1/2007 |
| WO | WO 2014/138139 A1 | | 9/2014 |
| WO | WO 2014/182248 A1 | | 11/2014 |

OTHER PUBLICATIONS

Karlgard, C. C. S., et al. "In vitro uptake and release studies of ocular pharmaceutical agents by silicon-containing and p-HEMA hydrogel contact lens materials." International Journal of Pharmaceutics 257.1 (2003): 141-151. (11 pages in English).

Ciolino, Joseph B., et al. "Contact Lenses for Drug Delivery." Seminars in Ophthalmology. vol. 24. No. 3. (2009): 156-160. (6 pages in English).

Lebrecht, Antje, et al. "Surface-Enhanced Laser Desorption/Ionisation Time-of-Flight Mass Spectrometry to Detect Breast Cancer Markers in Tears and Serum." Cancer Genomics—Proteomics 6.2 (2009): 75-84. (9 pages in English).

Peng, Cheng-Chun, et al. "Extended cyclosporine delivery by silicone-hydrogel contact lenses." Journal of Controlled Release 154.3 (2011): 267-274. (8 pages in English).

Ciolino, Joseph B., et al. "A Prototype Antifungal Contact Lens." Investigative Ophthalmology & Visual Science 52.9 (Aug. 2011): 6286-6291. (6 pages in English).

Salvisberg, Cindy, et al. "Exploring the human tear fluid: discovery of new biomarkers in multiple sclerosis." Proteomics—Clinical Applications 8.3-4 (2014): 185-194. (10 pages in English).

Pieragostino, Damiana, et al. "Unraveling the molecular repertoire of tears as a source of biomarkers: beyond ocular diseases." Proteomics—Clinical Applications 9.1-2 (2015): 169-186. (18 pages in English).

* cited by examiner

CONTACT LENS FOR COLLECTING TEAR OR DELIVERING DRUG, AND METHOD FOR MANUFACTURING THE CONTACT LENS

CROSS-REFERENCE TO RELATED APPLICATION

This application claims priority to Korean Patent Application No. 10-2016-0155809, filed on Nov. 22, 2016, and all the benefits accruing therefrom under 35 U.S.C. § 119, the contents of which in its entirety are herein incorporated by reference.

BACKGROUND

1. Field

The present disclosure relates to a contact lens and a method for manufacturing the contact lens, and more particularly, to a contact lens, which may be directly worn on an eyeball to collect tear or deliver a drug, and a method for manufacturing the contact lens.

[Description about National Research and Development Support]

This study was supported by the Bio & Medical Technology Development program of Ministry of Science, ICT and Future Planning, Republic of Korea (Project No. 1711038180) under the superintendence of National Research Foundation of Korea.

2. Description of the Related Art

For modern people with the eyes overtaxed, the health of eyes is an important factor to maintain a healthy life.

In particular, the tear is composed of inorganic electrolytes such as calcium and magnesium and organic components such as glucose, lactic acid, protein and lipid, and thus the health state may be measured by analyzing the concentration and components of the tear.

In the existing technique, a method for giving an artificial stimulation to an eyeball to collect tear and forcibly extracting tear through a fine tube has been used.

However, in this existing technique, the components of tear serving as indexes representing various health states such as glucose may be diluted or changed, and thus the components of tear may not be accurately analyzed.

In addition, if the eye suffers from any disease, a drug should be successively injected thereto for treatment.

However, it is not easy to wear any separate device for injecting a drug on the eye which is a very sensitive organ, and thus eye drops are generally applied onto the eye intermittently using a dropper. In fact, there is an investigation result revealing that 67 to 78% of glaucoma patients use a dropper without any medical effect.

SUMMARY

The present disclosure is directed to providing a contact lens, which may be worn on the eye without any burden to collect tear or deliver a drug and be used for a clinical purpose and for a long time, and a method for manufacturing the contact lens.

In one aspect of the present disclosure, there is provided a contact lens, comprising: an inner lens placed on an eyeball; an outer lens provided at an outer side of the inner lens to overlap the inner lens; and a plurality of pillars disposed between the inner lens and the outer lens to form a space (hereinafter, a "chamber") between the inner lens and the outer lens, wherein the contact lens has a plurality of interfacing ports for connecting the chamber with an outside.

In an embodiment, the interfacing port may have a tear inlet, and a coating layer having a hydrophilic property may be formed at a surface of the chamber so that external tear flows into the chamber through the tear inlet by means of a capillary phenomenon.

In an embodiment, the interfacing port may include a plurality of tear inlets, and a plurality of air outlets for allowing the air in the chamber to flow out as the tear may flow into the chamber, wherein the tear inlet may be formed along an outer circumference of the outer lens, and the air outlet may be formed closer to a center of the outer lens in comparison to the tear inlet.

In an embodiment, the tear inlet may be opened in an extension direction of the outer lens and the inner lens.

In an embodiment, the interfacing port may have a drug outlet, and a drug filled in the chamber may be delivered to the eyeball by means of dispersion.

In an embodiment, the drug may be filled in the chamber as a mixture with a medium, and the drug may flow out of the chamber by means of dispersion caused by a difference in concentration of the drug at an inside and an outside of the chamber.

In an embodiment, the drug outlet may be opened toward an inner surface of the inner lens to face the eyeball.

In an embodiment, the drug outlet may be elongated in a radial direction of the inner lens.

In an embodiment, a center portion of the contact lens may be free from the pillar to form a visual field region for ensuring a visual field of a user.

In an embodiment, the center portion of the outer lens may be cut off so that only the inner lens remains in the visual field region.

In another aspect of the present disclosure, there is provided a method for manufacturing a contact lens, the method comprising: forming an outer lens having a plurality of pillars formed at an inner surface thereof; forming an inner lens having a smooth surface; treating the outer lens and the inner lens with plasma; and adhering the outer lens and the inner lens to overlap each other.

In an embodiment, the method for manufacturing a contact lens may further comprise: depositing a polymer film on the inner surface of the outer lens; and depositing a polymer film on an outer surface of the inner lens, wherein the polymer film may have a hydrophilic property by means of the plasma treatment, and the outer lens and the inner lens may be adhered to each other by means of an adhesive.

In an embodiment, the outer lens and the inner lens may be made of silicon rubber, and the outer lens and the inner lens may have adhesion by means of the plasma treatment and thus are adhered to each other without a separate adhesive.

DETAILED DESCRIPTION

Hereinafter, embodiments of the present disclosure will be described with reference to the accompanying drawings. Though the present disclosure is explained based on the embodiments depicted in the drawings of the present disclosure, the technical features, essential configurations and operations of the present disclosure are not limited thereto.

Figure 1:
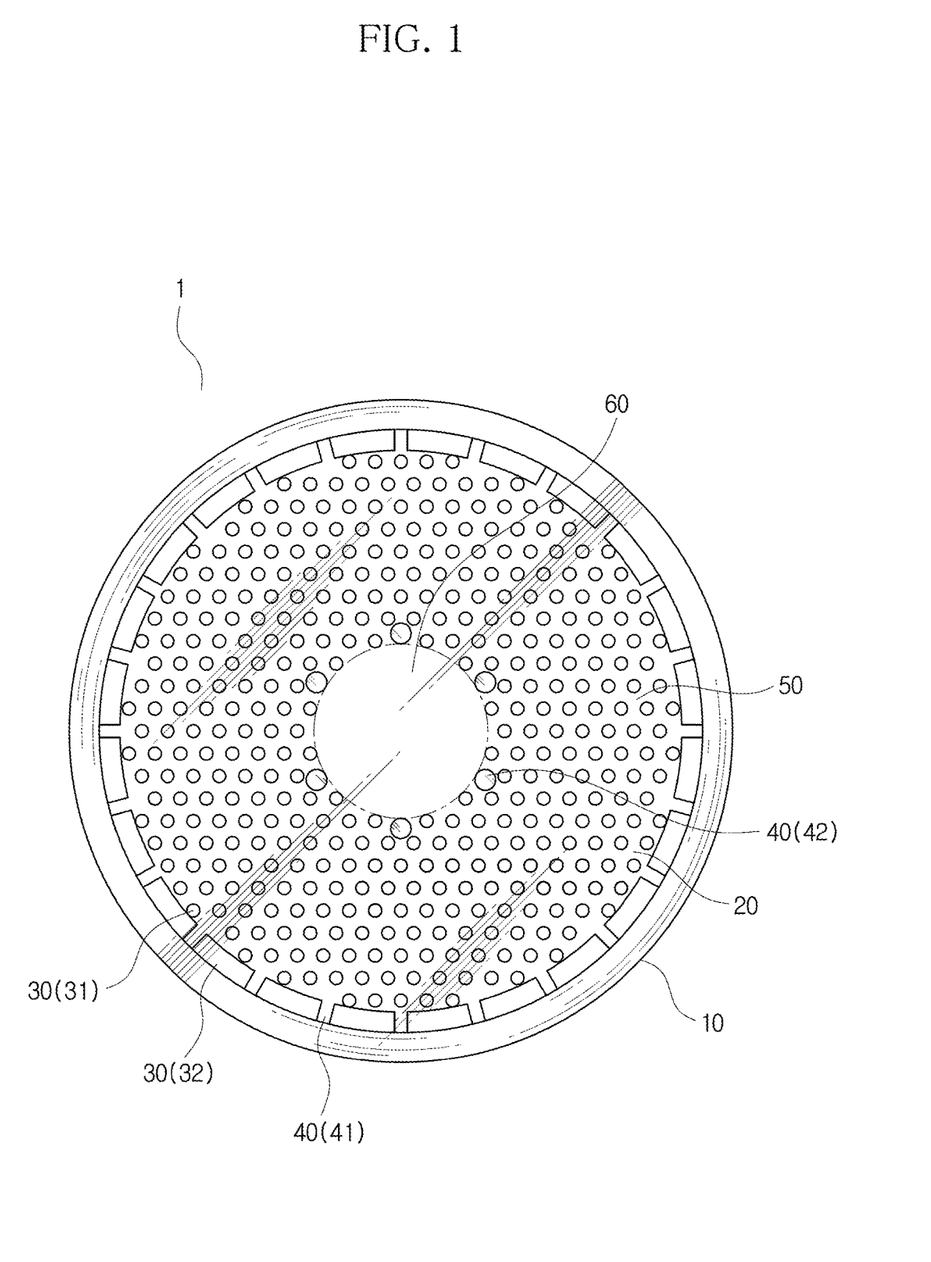
FIG. 1 is a front view showing a contact lens according to an embodiment of the present disclosure.
Figure 2:
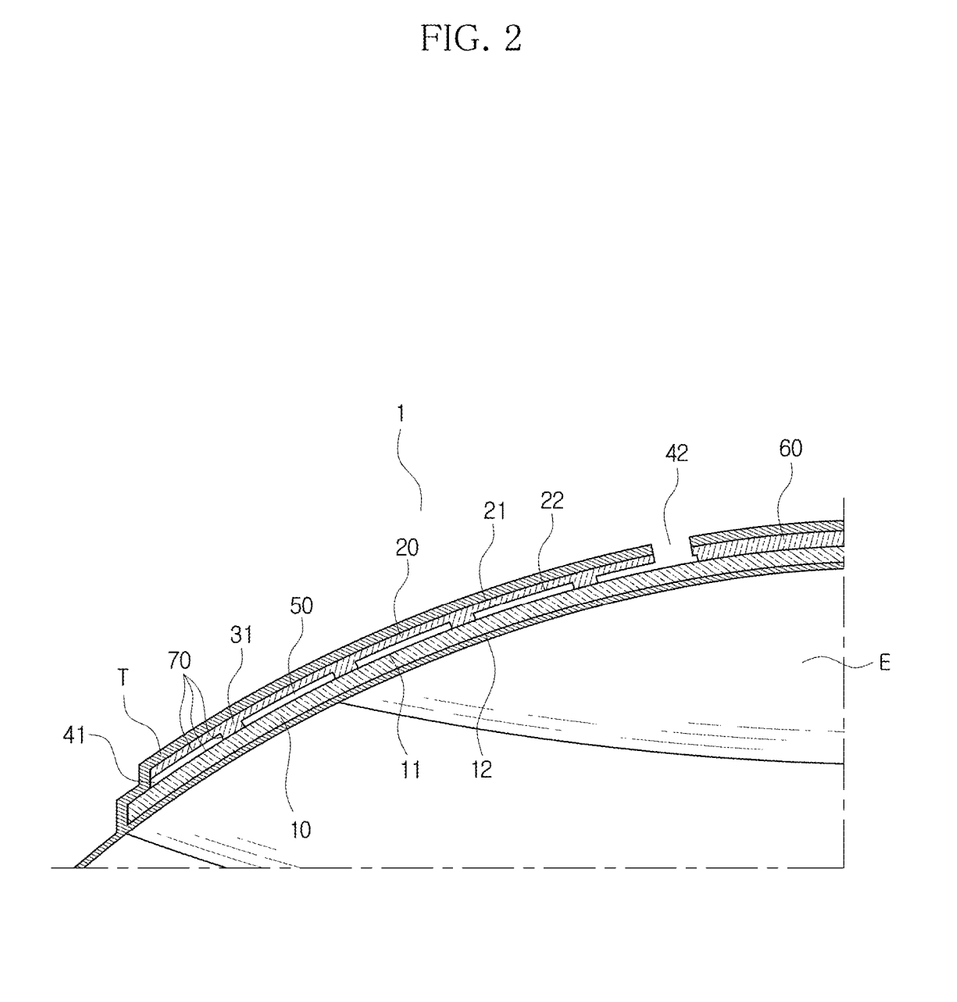
FIG. 2 is a cross-sectioned view showing the contact lens of FIG. 1.

FIG. 1 is a front view showing a contact lens 1 according to an embodiment of the present disclosure, and FIG. 2 is a cross-sectioned view showing the contact lens 1 of FIG. 1.

As shown in FIGS. 1 and 2, the contact lens 1 of this embodiment includes an inner lens 10 placed on an eyeball E, and an outer lens 20 provided at an outer side of the inner lens 10 to overlap the inner lens 10.

The inner lens 10 has an inner surface 12 and an outer surface 11 formed smooth with a soft curved shape corresponding to the shape of the eyeball E. The outer lens 20 has a soft curved shape to be substantially parallel to the inner lens 10 and has a smooth outer surface 21. As explained later, in this embodiment, a plurality of pillars 30 is formed integrally with the outer lens 20 to extend from an inner surface 22 of the outer lens 20, but the inner surface 22 of the outer lens 20 free from the pillar 30 has a smooth surface.

In this embodiment, an area of the outer lens 20 is smaller than an area of the inner lens 10, and the outer lens 20 and the inner lens 10 have concentric circular shapes.

The plurality of pillars 30 is formed between the inner lens 10 and the outer lens 20, thereby forming a space (hereinafter, called a "chamber") 50 between the inner lens 10 and the outer lens 20.

Referring to FIG. 1, the plurality of pillars 30 includes micro pillars 31 having a small cylindrical shape and evenly disposed over the entire area of the outer lens 20, and support pillars 32 intermittently formed at regular intervals along the periphery of the outer lens 20. The support pillar 32 is formed long to have a predetermined length greater than the micro pillar 31, thereby enhancing the adhesion between the outer lens 20 and the inner lens 10 adhered to each other.

As shown in FIG. 1, a plurality of interfacing ports 40 is formed in the contact lens 1 to communicate the chamber 50 with the outside.

The contact lens 1 of this embodiment may collect tear from the eyeball E. For this, the interfacing port 40 of this embodiment has a tear inlet 41 and an air outlet 42.

The tear inlet 41 is formed between two support pillars 32 adjacent to each other, and a plurality of tear inlets 41 is formed over the entire outer circumference of the outer lens 20.

The tear inlets 41 are formed over the entire outer circumference of the outer lens 20 in order to solve any inconvenience that a user should always dispose the contact lens 1 in a specific direction for wearing. Due to the physical structure of a human, tear is generally collected at a lower side of the eyeball (a lower side in FIG. 1), and thus, if the contact lens 1 is worn on the eyeball, tear will mostly flow into the chamber 50 through several tear inlets 41 disposed at a lower side, among the plurality of tear inlets 41.

In this embodiment, as shown in FIG. 2, the tear inlet 41 is opened in an extension direction of the outer lens 20 and the inner lens 10. By doing so, the tear inlet 41 easily comes into contact with the tear collected at a lower side of the eye.

The air outlet 42 of this embodiment is formed at the outer lens 20, and the plurality of air outlets 42 is opened toward the outer surface 21 of the outer lens 20.

The air outlet 42 is disposed close to a center of the outer lens 20 which is relatively dry, so that air in the chamber 50 flows out, thereby allowing the tear to easily flow into the chamber 50.

In this embodiment, it should be understood that the tear inlet 41 and the air outlet 42 are named to express their intended functions.

As shown in FIG. 2, if the contact lens 1 is worn on the eyeball E, the tear T surrounds the entire surface of the contact lens 1 to form a thin film (see a gray portion in FIG. 2). Thus, for example, even though any interfacing port 40 is called the tear inlet 41, this interfacing port 40 may partially or temporarily serve as an air outlet depending on its location or situation.

In this embodiment, a fine gap is formed between the outer lens 20 and the inner lens 10 and a kind of fine channel is formed in the chamber 50 by means of the pillars 32. Thus, a capillary phenomenon occurs due to the fine channel, and so the tear flows into the chamber 50.

Figure 3:
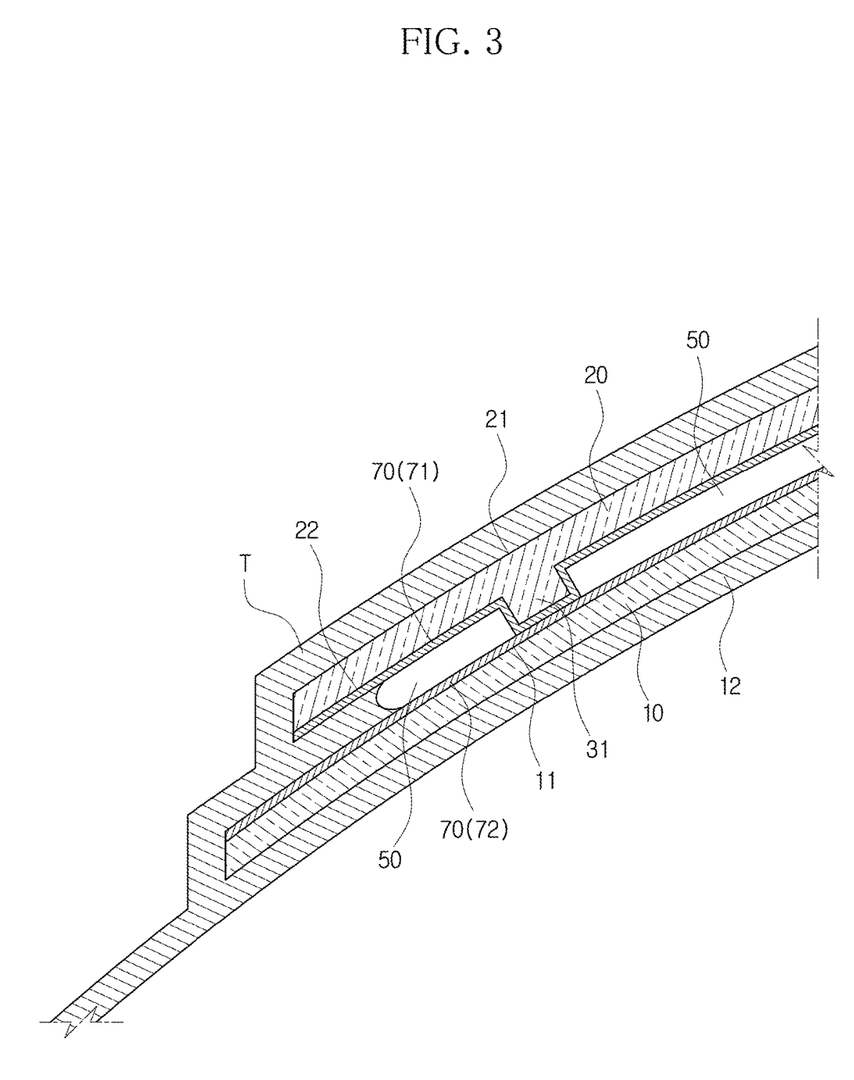
FIG. 3 is an enlarged view showing a part of FIG. 2.

FIG. 3 is an enlarged view showing a part of FIG. 2.

As shown in FIG. 3, the surface of the chamber 50 is surrounded by a coating layer 70 with a hydrophilic property.

In this embodiment, in order to form the coating layer 70 with a hydrophilic property, plasma treatment is used.

Figure 4:
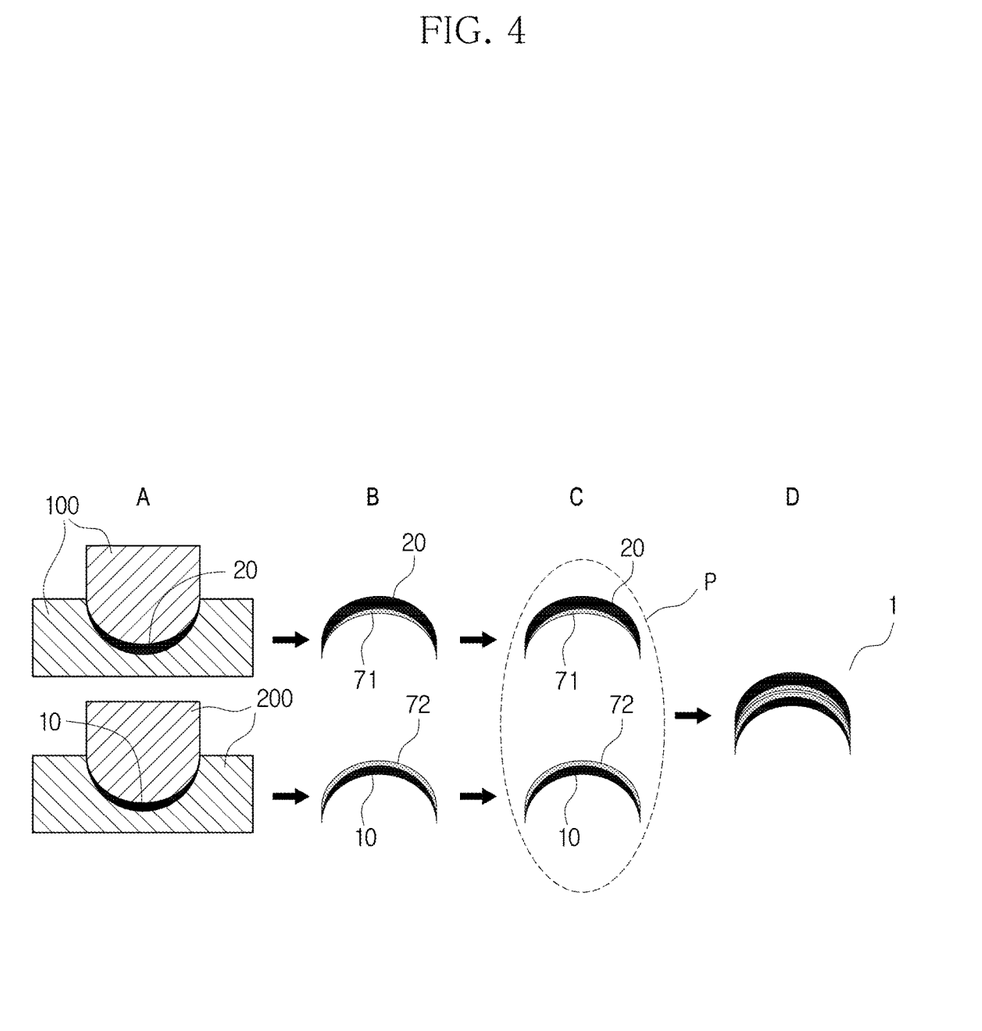
FIG. 4 is a diagram for illustrating a method for manufacturing the contact lens of FIG. 1.

FIG. 4 is a diagram for illustrating a method for manufacturing the contact lens 1 of FIG. 1.

As shown in FIG. 4, the outer lens 20 is formed using a mold 100, and the inner lens 10 is formed using a mold 200 (A). Though not shown in detail, the mold 100 is configured to form the pillars 30 and the interfacing ports 40 at desired locations in desired directions along with the outer lens 20 (the mold 200 is also configured in this way).

Next, a polymer film 71 is deposited on the inner surface 22 of the outer lens 20, and a polymer film 72 is deposited on the outer surface 11 of the inner lens 10 (B).

It is known in the art that the polymer surface may be modified to have a hydrophilic property by means of plasma treatment. In this embodiment, the outer lens 20 and the inner lens 10 shaped as above are treated with plasma so that the polymer films 71, 72 have a hydrophilic property (C).

In more detail, the polymer films 71, 72 of this embodiment are made of, for example, parylene-C. The polymer films 71, 72 are plasma-treated with 100 sccm of oxygen at 300 W for 5 minutes to have a hydrophilic property.

After that, the adhesive is coated on an end surface of the pillar 30, and the outer lens 20 and the inner lens 10 are placed to overlap each other and are then adhered (D).

In this method, it is possible to form the chamber 50 surrounded by the coating layer 70 made of a hydrophilic polymer.

Referring to FIG. 3 again, the tear T mostly composed of water comes into contact with the hydrophilic coating layer 70 of the chamber 50 at the tear inlet 41, and the tear spreads wide along the coating layer 70 due to its surface tension and cohesiveness and flows into the chamber 50 by means of a capillary phenomenon.

After a predetermined time, the tear T flowing into the chamber 50 through the tear inlet 41 is filled in the entire area of the chamber 50 by means of a capillary phenomenon of the coating layer 70 and the fine channel.

After a sufficient time passes, the contact lens 1 may be collected, and tear may be extracted from the chamber 50 and then analyzed.

The contact lens 1 of this embodiment is worn on the eyeball, and tear is naturally collected without any stimulation. Thus, it is possible to easily collect high-quality tear for tear analysis.

Meanwhile, since the contact lens 1 of this embodiment is directly worn at the front of the eyeball of the user, the entire portion, or at least a central portion, of the outer lens 20 and the inner lens 10 is made of a transparent material, thereby forming a visual field region 60 at the center portion of the contact lens 1.

In the visual field region 60, the pillar 30 is not formed, and the outer lens 20 and the inner lens 10 directly come into contact with each other (in this embodiment, two coating layers 71, 72 are in contact), so that an optical disturbance is not caused by the pillar 30.

However, since two lenses, namely the outer lens 20 and the inner lens 10, overlap each other in the visual field region 60, the sight of the user may be partially deterred.

According to another embodiment of the present disclosure, a single-layer lens is formed in the visual field region to ensure the sight of the user.

Figure 5:
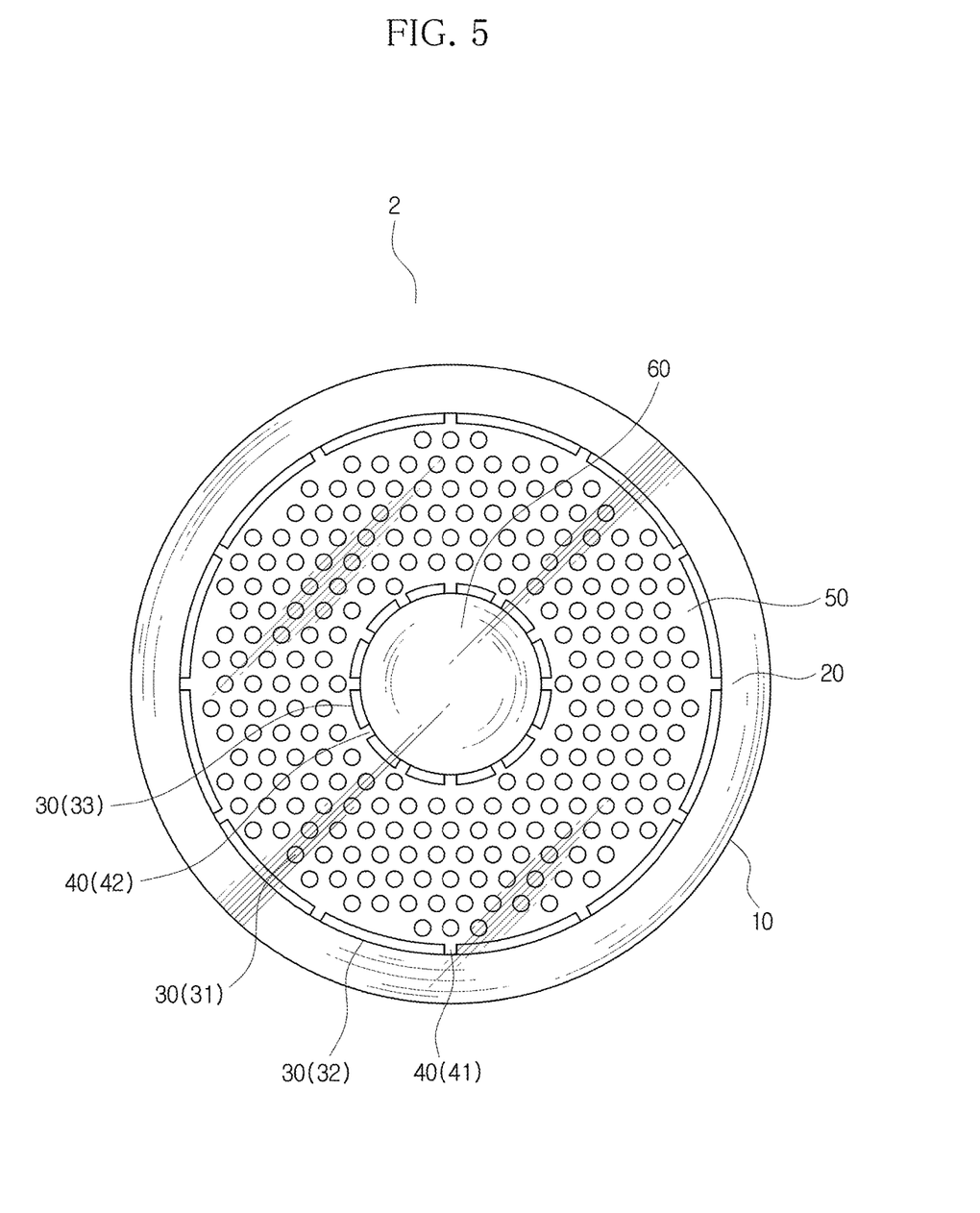
FIG. 5 is a front view showing a contact lens according to another embodiment of the present disclosure.
Figure 6:
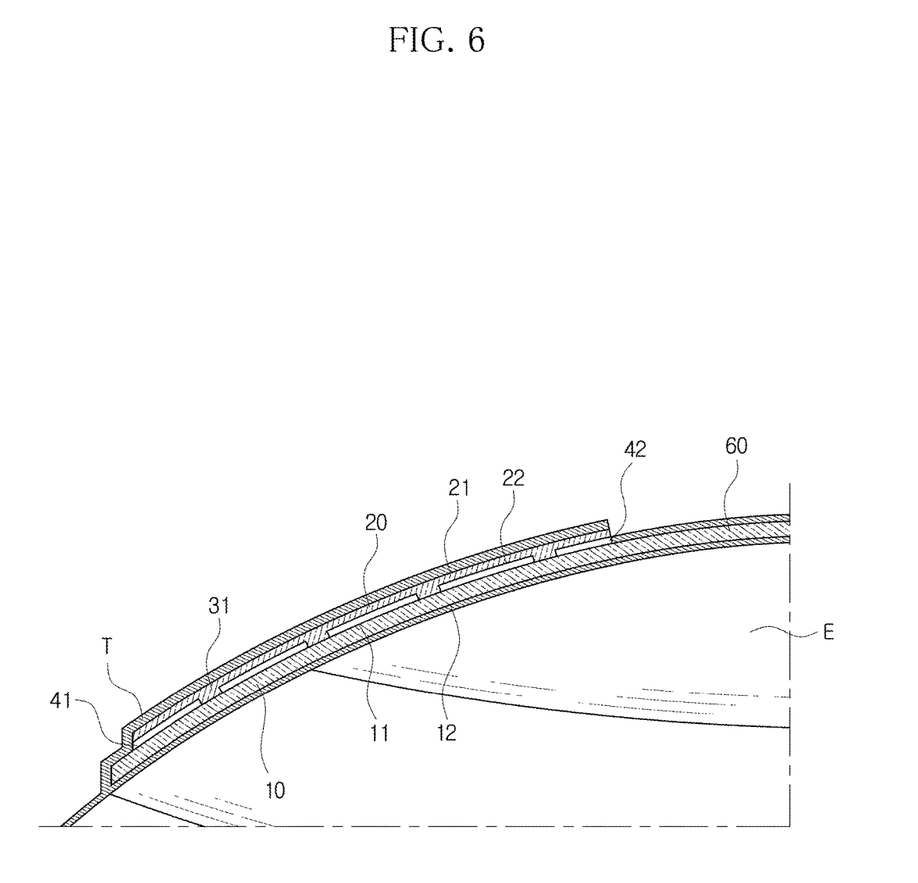
FIG. 6 is a cross-sectioned view showing the contact lens of FIG. 5.

FIG. 5 is a front view showing a contact lens 2 according to another embodiment of the present disclosure, and FIG. 6 is a cross-sectioned view showing the contact lens 2 of FIG. 5.

As shown in FIGS. 5 and 6, the contact lens 2 of this embodiment is different from that of the former embodiment in the point that the center portion of the outer lens 20 is circularly cut off so that only the inner lens 10 remains in the visual field region 60. The coating layer 72 coated on the outer surface 11 of the inner lens 10 may also be removed in the visual field region 60. A gray portion in FIG. 6 represents the tear T surrounding the contact lens 2.

In this embodiment, since only a single-layer lens (the inner lens 10) is present in the visual field region 60, a clearer sight may be provided to the user.

In this embodiment, since the center portion of the outer lens 20 is circularly cut off, support pillars 33 extending longer than the micro pillars 31 are formed along a rim portion of the visual field region 60 in order to enhance a support force of the connection portion.

The air outlet 42 is formed between support pillars 33 adjacent to each other and is also opened in the extension direction of the outer lens 20 and the inner lens 10, similar to the tear inlet 41.

The contact lens 2 of this embodiment collects the tear in the chamber 50 by means of a capillary phenomenon, similar to the contact lens 1 of the former embodiment. The principle and configuration for collecting tear are substantially identical to those of the former embodiment.

Among the reference symbols depicted in FIGS. 5 and 6 but not explained, all reference symbols identically used in FIGS. 1 to 4 have the same functions as in FIGS. 1 to 4 and thus are not described in detail again. This is also applied to other figures likewise.

The contact lens of this embodiment naturally collects tear by means of a capillary phenomenon without any driving unit. The time and speed of filling tear in the chamber 50 by means of a capillary phenomenon may be controlled by adjusting a width of the tear inlet 41, height and size of the pillars 30, distance between the pillars 30, and the number of pillars 30.

Figure 7:
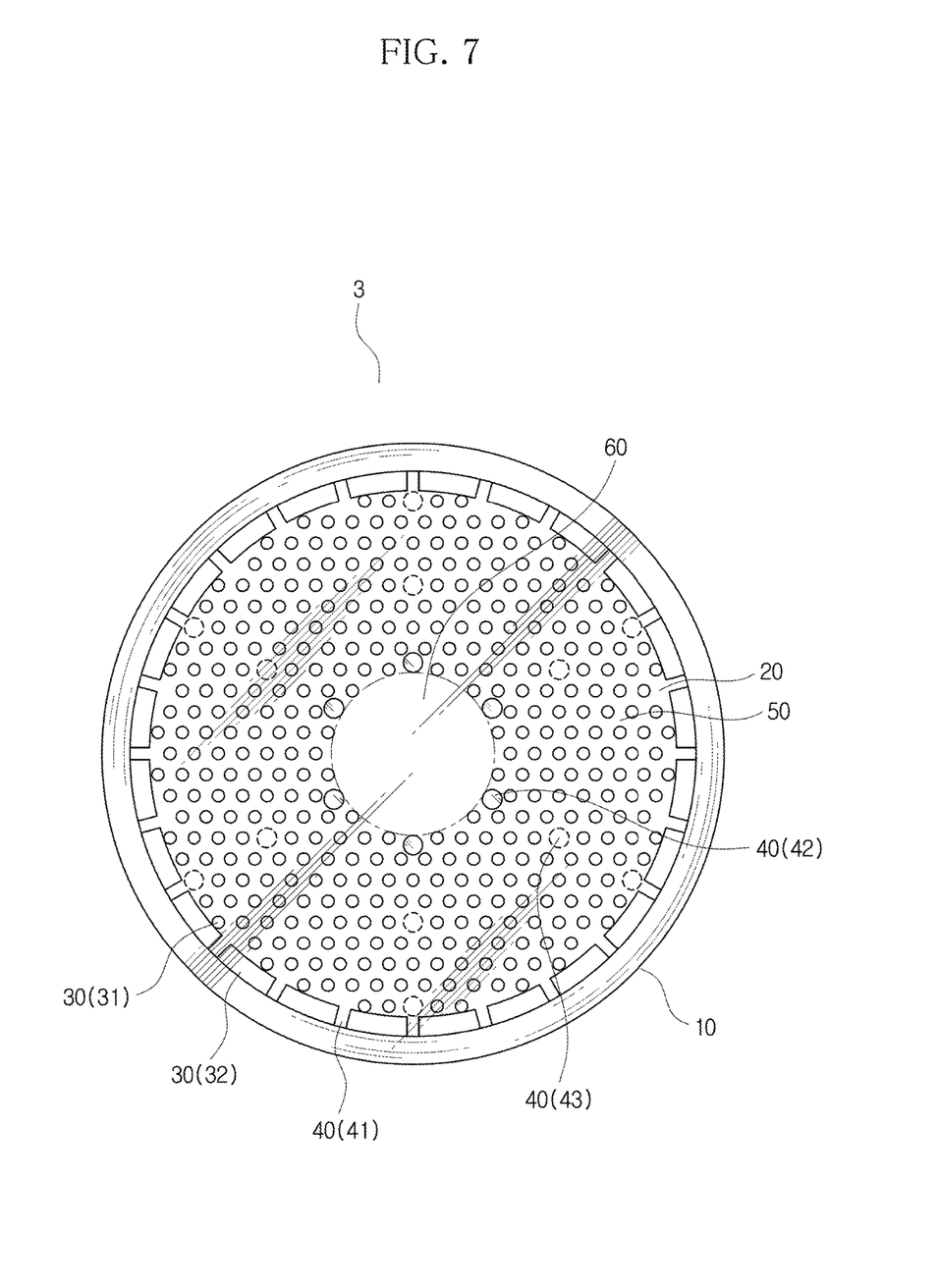
FIG. 7 is a front view showing a contact lens according to another embodiment of the present disclosure.
Figure 8:
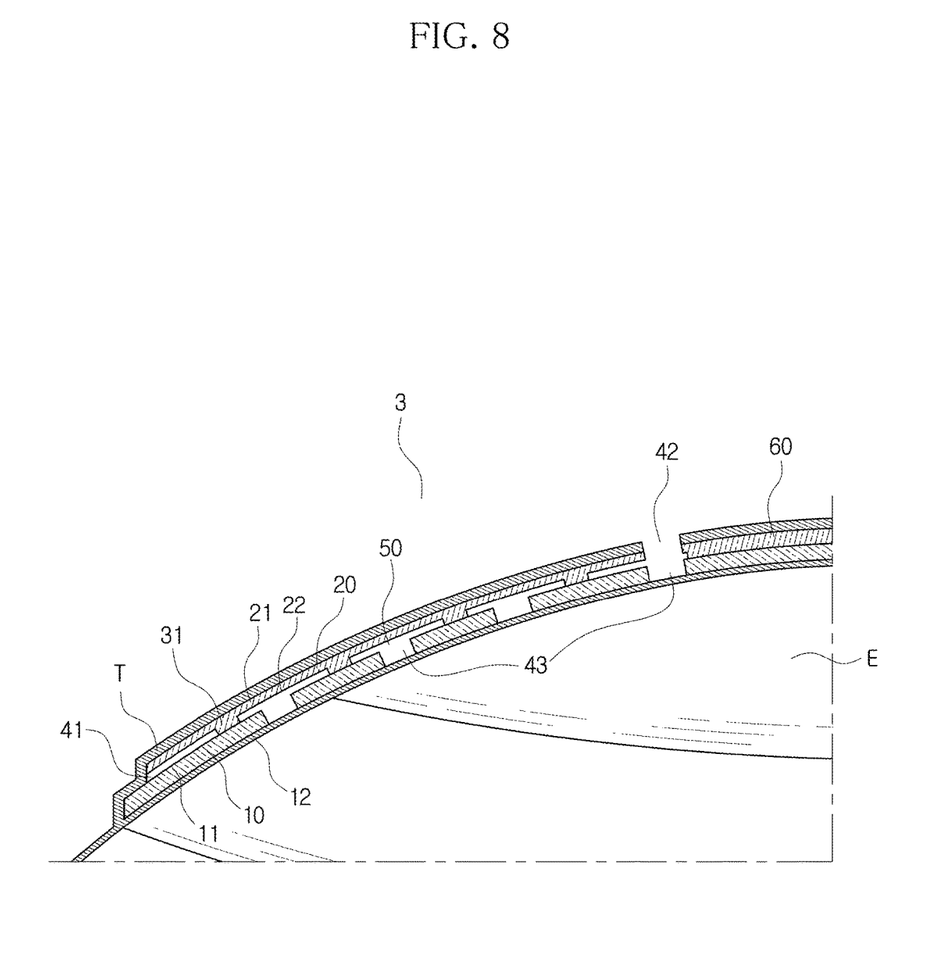
FIG. 8 is a cross-sectioned view showing the contact lens of FIG. 7.
Figure 9:
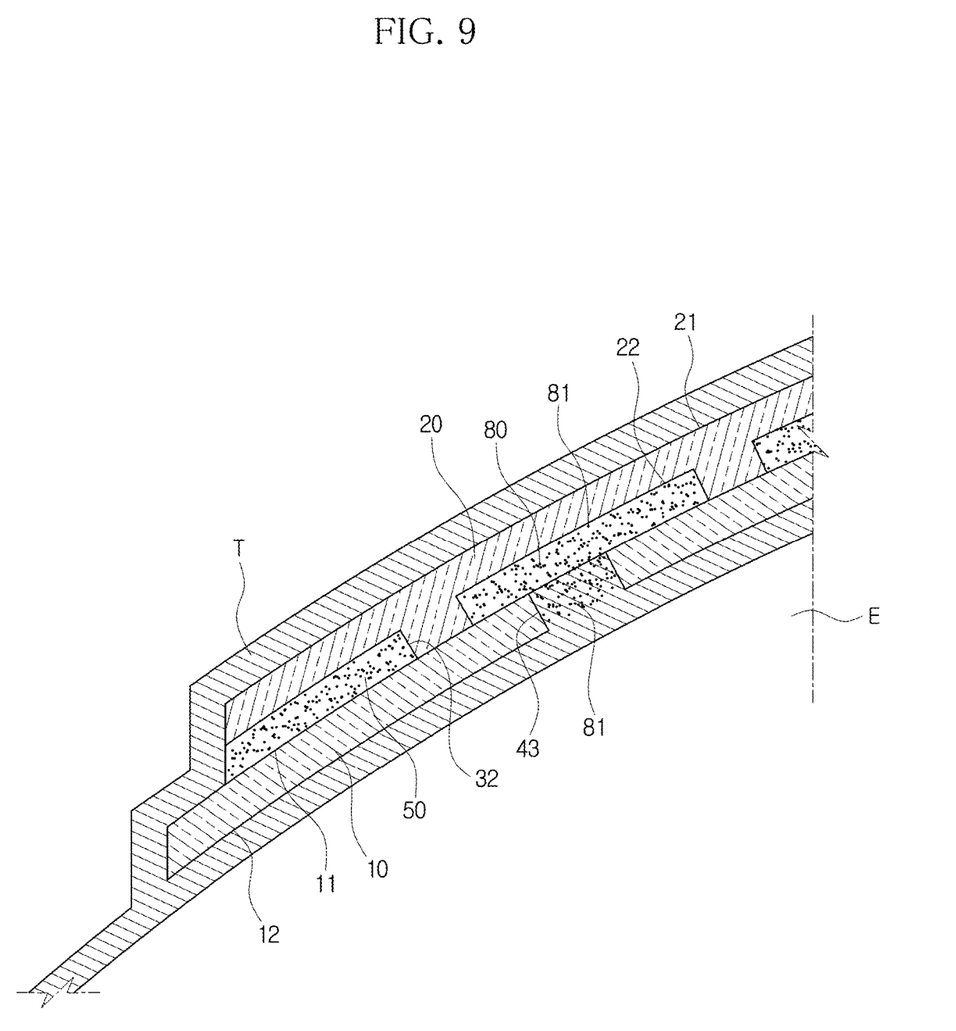
FIG. 9 is an enlarged view showing a part of FIG. 8.

FIG. 7 is a front view showing a contact lens 3 according to another embodiment of the present disclosure, FIG. 8 is a cross-sectioned view showing the contact lens 3 of FIG. 7, and FIG. 9 is an enlarged view showing a part of FIG. 8.

The contact lens 3 of this embodiment is intended to deliver a drug to the eyeball E and is different from that of the former embodiment in the point that a drug 51 is filled in the chamber 50 and also the interfacing port 40 has a drug outlet 43 for emitting the drug.

In addition, a hydrophilic or non-hydrophilic coating layer may be formed in the chamber 50 as necessary. However, it is not needed to introduce tear T into the contact lens 3 of this embodiment from the outside, and thus in the contact lens 3 of this embodiment, a separate hydrophilic coating layer is not formed in the chamber 50, and the pillars 30 and the inner lens 10 are adhered to each other to couple the outer lens 20 and the inner lens 10 to each other.

Referring to FIG. 4 again, the contact lens 3 of this embodiment may be manufactured without performing the process B. In the contact lens 3 of this embodiment, the outer lens 20 and the inner lens 10 are made of silicon rubber.

The silicon rubber is known as having an adhesion to the same silicon rubber when being treated with plasma. Therefore, in this embodiment, the outer lens 20 and the inner lens 10 are treated with plasma (C), so that the outer lens 20 and the inner lens 10 are adhered to each other without any separate adhesive.

As well shown in FIG. 9, the chamber 50 is filled with a medium 80 (a light gray portion in FIG. 9), and the hydrogel 80 is mixed with a drug 81. The medium is a material containing a drug and also capable of delivering drug molecules to tear, and for example, hydrogel and poly lactide-co-glycolide (PLGA) may be used as the medium.

The medium 80 comes into contact with the tear T at the drug outlet 43, and due to a difference in drug concentration between the medium 80 and the tear T, molecules of the drug 81 flow out of the chamber 50 and flow into the tear T by means of dispersion. Due to the tear T forming a film at the surface of the eyeball, the drug is delivered to the eyeball E to be evenly spread over the entire eyeball E.

In this embodiment, the drug outlet 43 is opened toward the inner surface 12 of the inner lens 10 so that the drug is evenly delivered to the entire eyeball E, and a plurality of drug outlets 43 (a dotted line in FIG. 7) is distributed with a predetermined pattern over the entire area of the outer lens 20.

In this embodiment, the contact lens 3 has interfacing ports 40 serving as filling openings 41, 42, which correspond to the tear inlet 41 and the air outlet 42 of the contact lens 1.

The filling openings 41, 42 may be used for injecting the medium 80 containing a drug into the chamber 50 of the contact lens 3.

However, while the contact lens 3 is in use, a medium may not be filled separately and the filling openings 41, 42 may be closed. It is also possible that the filling openings 41, 42 are not closed but the contact lens 3 is used so that the filling openings 41, 42 serve as a drug outlet for emitting the drug.

It may also be conceived that a medium such as hydrogel is cured into a lens form to deliver a drug to the eyeball. However, in this method, hydrogel is easily deformed to deteriorate durability, and the drug is diffused over the entire eyeball and thus is consumed too rapidly, which limits the kinds of available drug and also shortens the life span of the drug.

In this embodiment, since the medium is filled in a lens which is kept in a specific shape, good durability is ensured, and also an injection rate or the like of the drug may be controlled by adjusting a location or entire area of the drug outlet 43.

Figure 10A:
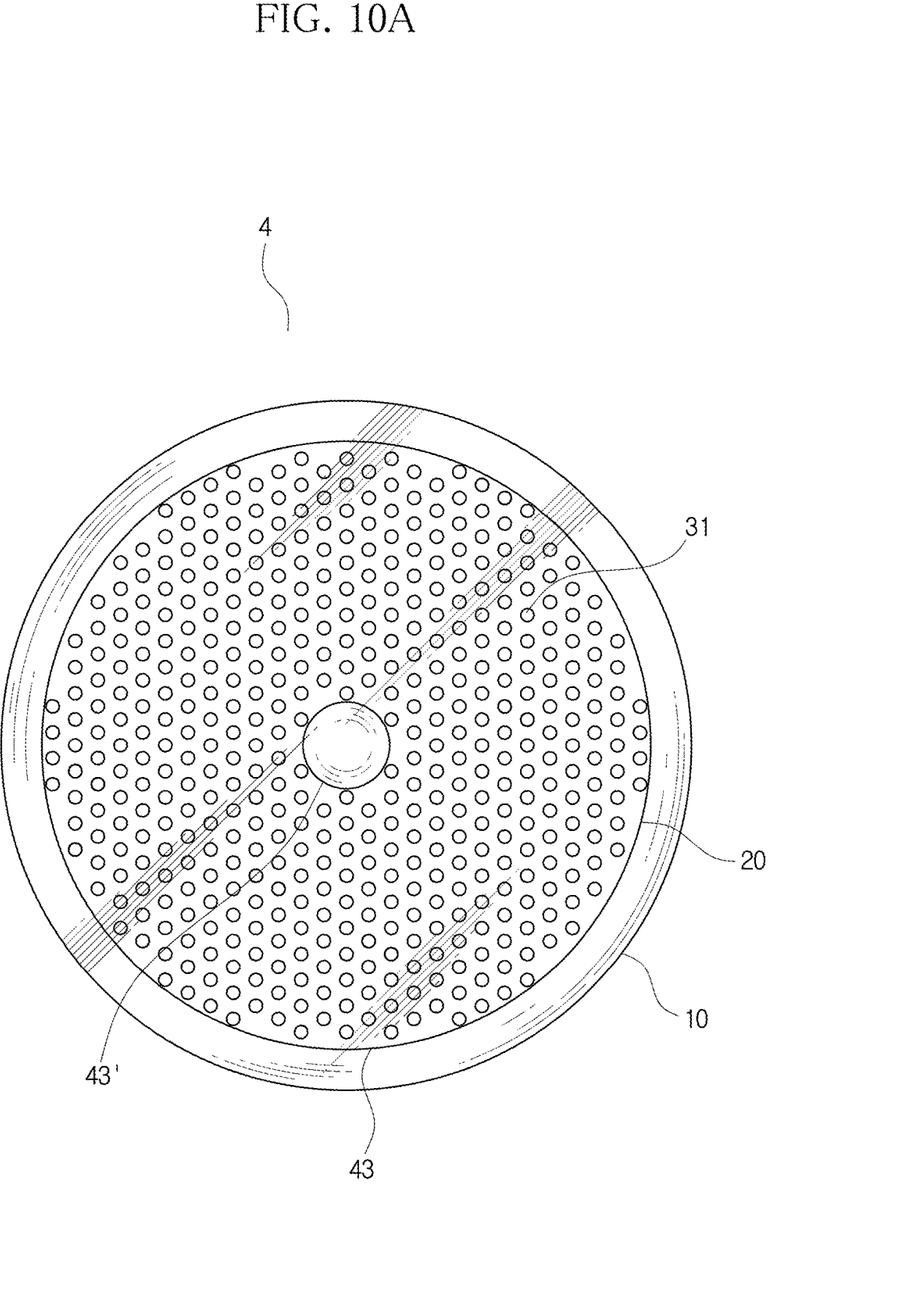
FIGS. 10A and 10B are front views showing contact lenses according to other embodiments of the present disclosure.
Figure 10B:
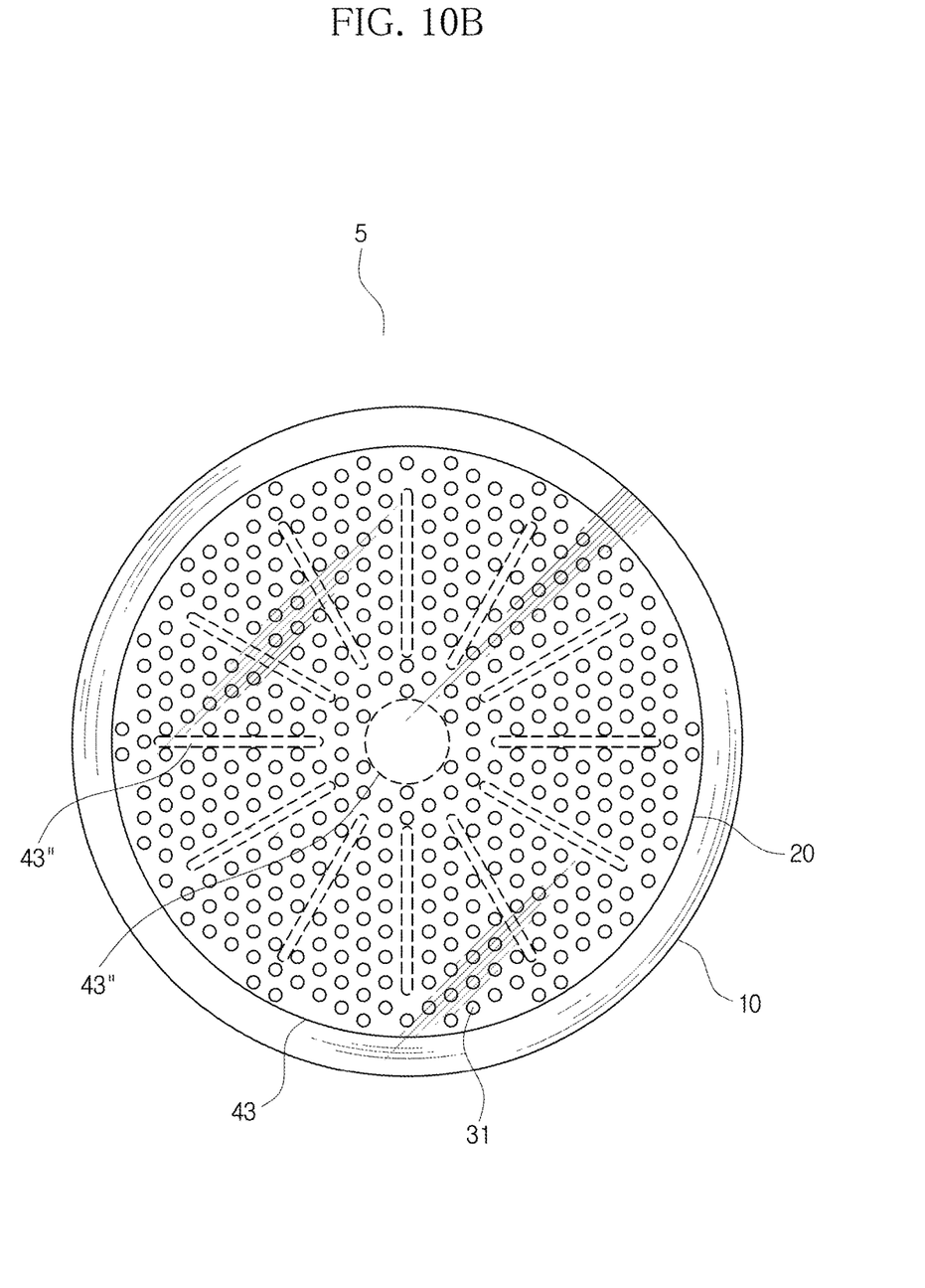

FIGS. 10A and 10B are front views showing contact lenses according to other embodiments of the present disclosure.

As shown in FIG. 10A, the contact lens 4 of this embodiment does not include a drug outlet which is formed in the inner lens 10 to face the eyeball. Instead, the inner lens 10 and the outer lens 20 are adhered just by means of the micro pillars 31 without using the support pillars, and then the center portion of the outer lens 20 is cut off. Alternatively, the center portion of the inner lens 10 may also be cut off for delivering the drug to the eyeball directly. In this way, both the outer circumference and the inner circumference of the outer lens 20 may serve as drug outlets 43, 43'.

Further, as shown in FIG. 10B, a contact lens 5 according to an embodiment further has a slit-type drug outlet 43" (a dotted line in FIG. 10B) formed in the inner lens 10 to face the eyeball and elongated in a radial direction of the inner lens 10, in addition to the configuration of the contact lens 4.

The contact lenses according to the embodiments depicted in FIG. 7, FIG. 10A and FIG. 10B are different in drug dispersion patterns and rates.

As described above, the contact lens for delivering a drug may freely adjust drug delivery distribution and rate by changing the location, shape and total area of the drug outlets in various ways.

In the embodiment of the present disclosure, the contact lens has a smooth surface without any unevenness, and thus a user may wear the contact lens on the eye for a long time without any burden, similar to general contact lenses.

In addition, the contact lens according to the embodiment of the present disclosure collects tear or delivers a drug by means of a continuous and consistent phenomenon such as a capillary phenomenon or dispersion without any separate driving unit, thereby ensuring high productivity and excellent efficiency.

In particular, since the contact lens is manufactured by means of a molding process using a mold, it is possible to easily adjust locations, patterns and numbers of interfacing ports and pillars, thereby allowing inexpensive production with high clinical efficiency.

What is claimed is:

1. A contact lens, comprising:
an inner lens configured to be placed on an eyeball;
an outer lens provided at an outer side of the inner lens to overlap the inner lens; and
a plurality of pillars disposed between the inner lens and the outer lens to form a chamber between the inner lens and the outer lens,
wherein the contact lens has a plurality of interfacing ports for connecting the chamber to an outside of the contact lens, including an interfacing port formed between two adjacent pillars disposed along an outer circumference of the outer lens,
wherein a center portion of the contact lens is free from the two adjacent pillars to form a visual field region for ensuring a visual field of a user, and
wherein the chamber is configured to collect fluid of a tear drawn into the chamber by plural tear inlet ports of the plurality of interfacing ports.

2. The contact lens according to claim 1, further comprising a coating layer, having a hydrophilic property, formed at a surface of the chamber so that the tear is drawn into the chamber by the interfacing port through a capillary phenomenon.

3. The contact lens according to claim 2,
wherein the plurality of interfacing ports further comprise a plurality of air outlets configured to provide respective outlets for air in the chamber to flow out as the tear flows into the chamber, and
wherein the plural tear inlet ports are formed along an outer circumference of the outer lens, and the plurality of air outlets are formed closer to an axial center of the outer lens than the plural tear inlet ports.

4. The contact lens according to claim 3,
wherein the plural tear inlet ports are each open, to the outside of the contact lens, in an extension direction of the outer lens and the inner lens.

5. The contact lens according to claim 3, wherein each of the plural tear inlet ports is formed between respective two adjacent pillars disposed along the outer circumference of the outer lens and is configured to draw the fluid of the tear into the chamber.

6. The contact lens according to claim 1, wherein the plurality of interfacing ports further comprise a drug outlet,
wherein a drug filled in the chamber is delivered to the eyeball through dispersion using the drug outlet.

7. The contact lens according to claim 6,
wherein the drug is filled in the chamber as a mixture with a medium, and
wherein the drug flows out of the chamber through dispersion caused by a difference in concentration of the drug at an inside and an outside of the chamber.

8. The contact lens according to claim 6,
wherein the drug outlet is open, to the outside of the contact lens, toward an inner surface of the inner lens to face the eyeball.

9. The contact lens according to claim 8,
wherein the drug outlet is elongated in a radial direction of the inner lens.

10. The contact lens according to claim 1,
wherein the center portion of the outer lens is cut off so that only the inner lens remains in the visual field region.

11. A method for manufacturing a contact lens of claim 1, the method comprising:
forming the outer lens having the plurality of pillars formed at;
forming the inner lens having a smooth surface;
treating the outer lens and the inner lens with plasma; and
adhering the outer lens and the inner lens to overlap each other.

12. The method according to claim 11, further comprising:
depositing a polymer film on the inner surface of the outer lens; and
depositing a polymer film on an outer surface of the inner lens,
wherein the polymer film has a hydrophilic property due to the plasma treatment, and
wherein the outer lens and the inner lens are adhered to each other by an adhesive.

13. The method according to claim 11,
wherein the outer lens and the inner lens are made of silicon rubber, and
wherein the outer lens and the inner lens have adhesion due to the plasma treatment and thus are adhered to each other without a separate adhesive.

14. The contact lens according to claim 1, wherein the plurality of interfacing ports further comprise another interfacing port configured to provide an outlet for air in the chamber to flow out as the tear is drawn into the chamber, the other interfacing port being axially positioned with respect to the outer lens different from an axial position, with respect to the outer lens, of the interfacing port.

15. The contact lens according to claim 1, wherein the plurality of pillars include a plurality of micro pillars and a plurality of support pillars,
the plurality of support pillars are formed along the outer circumference of the outer lens, with a tear inlet of the plural tear inlet ports being formed between two adjacent support pillars of the plurality of support pillars,
the micro pillars are formed between an axial center of the outer lens and the outer circumference of the outer lens, and
the support pillars have lengths greater than those of micro pillars.

* * * * *